US010336900B2

(12) United States Patent
Pärssinen

(10) Patent No.: US 10,336,900 B2
(45) Date of Patent: *Jul. 2, 2019

(54) COMPOSITE MATERIALS COMPRISING A THERMOPLASTIC MATRIX POLYMER AND WOOD PARTICLES

(75) Inventor: Antti Pärssinen, Helsinki (FI)

(73) Assignee: ONBONE OY, Helsinki (FI)

(*) Notice: Subject to any disclaimer, the term of this patent is extended or adjusted under 35 U.S.C. 154(b) by 0 days.

This patent is subject to a terminal disclaimer.

(21) Appl. No.: 13/255,930

(22) PCT Filed: Mar. 11, 2010

(86) PCT No.: PCT/FI2010/050185
§ 371 (c)(1),
(2), (4) Date: Nov. 30, 2011

(87) PCT Pub. No.: WO2010/103186
PCT Pub. Date: Sep. 16, 2010

(65) Prior Publication Data
US 2012/0071590 A1 Mar. 22, 2012

(30) Foreign Application Priority Data
Mar. 11, 2009 (FI) .................... 20095251

(51) Int. Cl.
C08L 67/04 (2006.01)
C08L 97/02 (2006.01)
(Continued)

(52) U.S. Cl.
CPC ............ C08L 67/04 (2013.01); A43B 17/003 (2013.01); A61F 5/058 (2013.01); A61F 5/14 (2013.01);
(Continued)

(58) Field of Classification Search
CPC .......... C08L 97/02; C08L 67/04; A61L 15/12; A61L 15/14
(Continued)

(56) References Cited
U.S. PATENT DOCUMENTS 3,622,431 A 11/1971 Turcksin
3,921,333 A 11/1975 Clendinning et al.
(Continued)

FOREIGN PATENT DOCUMENTS

EP 0393003 A1 10/1990
EP 0407055 A1 1/1991
(Continued)

OTHER PUBLICATIONS

Balatinecz, J. J., et al., "Achievements in the utilization of poplar wood—guideposts for the future," Forestry Chronicle, 2001, 77, 265-269.*
(Continued)

Primary Examiner — Nicholas E Hill
(74) Attorney, Agent, or Firm — Oliff PLC

(57) ABSTRACT

The present invention concerns a novel low-temperature thermoplastic wood-biopolymer composite comprised of small wood particles and a polycaprolactone (PCL) homopolymer for use in medical procedures including orthopedic casting or splinting. The material is made from a thermoplastic composite that softens when heated to approximately 60° C., after which it can be formed directly on the patient. The composite then retains its shape as it cools down. The material is composed of epsilon caprolactone homopolymer reinforced with discontinuous short length wood particles.

27 Claims, 4 Drawing Sheets

(51) Int. Cl.
*A61L 15/12* (2006.01)
*A61L 15/14* (2006.01)
*A61F 5/058* (2006.01)
*A43B 17/00* (2006.01)
*A61F 5/14* (2006.01)
*A63B 71/12* (2006.01)

(52) U.S. Cl.
CPC ............ *A61L 15/12* (2013.01); *A61L 15/125* (2013.01); *A61L 15/14* (2013.01); *C08L 97/02* (2013.01); *A63B 2071/1258* (2013.01); *A63B 2209/00* (2013.01); *C08L 2201/06* (2013.01); *C08L 2203/02* (2013.01); *Y10T 428/249921* (2015.04)

(58) Field of Classification Search
USPC ................................................ 524/13; 602/7
See application file for complete search history.

(56) References Cited

U.S. PATENT DOCUMENTS

| | | | |
|---|---|---|---|
| 4,019,505 A | 4/1977 | Wartman | |
| 4,021,388 A | 5/1977 | Griffin | |
| 4,153,051 A | 5/1979 | Shippert | |
| 4,213,452 A | 7/1980 | Shippert | |
| 4,240,415 A | 12/1980 | Wartman | |
| 4,273,115 A | 6/1981 | Holland et al. | |
| 4,376,438 A | 3/1983 | Straube et al. | |
| 4,473,671 A | 9/1984 | Green | |
| 4,661,535 A | 4/1987 | Borroff et al. | |
| 5,417,904 A * | 5/1995 | Razi et al. | 264/129 |
| 5,827,905 A | 10/1998 | Grigat et al. | |
| 5,863,480 A | 1/1999 | Suwanda | |
| 5,969,089 A * | 10/1999 | Narayan et al. | 528/357 |
| 6,071,984 A * | 6/2000 | Grigat et al. | 523/128 |
| 6,124,384 A | 9/2000 | Shiraishi et al. | |
| 6,143,811 A | 11/2000 | Oda et al. | |
| 6,184,272 B1 | 2/2001 | Foelster et al. | |
| 6,479,002 B1 | 11/2002 | Becker et al. | |
| 6,780,359 B1 | 8/2004 | Zehner et al. | |
| 6,884,518 B2 | 4/2005 | Aho et al. | |
| 6,911,522 B2 | 6/2005 | Manfredi et al. | |
| 7,323,253 B2 * | 1/2008 | Isaksson et al. | 428/524 |
| 7,601,282 B2 | 10/2009 | Gleich et al. | |
| 7,988,905 B2 | 8/2011 | Hashiba et al. | |
| 2001/0030031 A1 | 10/2001 | Willemse | |
| 2002/0143083 A1 | 10/2002 | Korney | |
| 2002/0143282 A1 | 10/2002 | Grim et al. | |
| 2004/0028927 A1 | 2/2004 | Leckey et al. | |
| 2005/0137304 A1 | 6/2005 | Strand et al. | |
| 2006/0065993 A1 * | 3/2006 | Stucky | B29C 44/32 264/51 |
| 2006/0241216 A1 | 10/2006 | Varachez et al. | |
| 2007/0132133 A1 | 6/2007 | Hasegawa | |
| 2007/0243782 A1 | 10/2007 | Takasu et al. | |
| 2007/0259584 A1 * | 11/2007 | Whitehouse | B27N 3/00 442/417 |
| 2007/0264460 A1 | 11/2007 | Del Tredici | |
| 2007/0287795 A1 | 12/2007 | Huda et al. | |
| 2008/0015285 A1 | 1/2008 | Oriani | |
| 2008/0032125 A1 | 2/2008 | Terasawa et al. | |
| 2008/0103423 A1 | 5/2008 | Nieberding | |
| 2008/0145656 A1 | 6/2008 | Jung | |
| 2008/0154164 A1 | 6/2008 | Sheehan et al. | |
| 2008/0241509 A1 | 10/2008 | Lai | |
| 2008/0262400 A1 | 10/2008 | Clark et al. | |
| 2008/0319362 A1 | 12/2008 | Joseph | |
| 2009/0036575 A1 | 2/2009 | Gardner et al. | |
| 2009/0105378 A1 | 4/2009 | Mukawa et al. | |
| 2009/0236766 A1 | 9/2009 | Rust et al. | |
| 2010/0093890 A1 | 4/2010 | Ataka et al. | |
| 2010/0136324 A1 | 6/2010 | Ohno et al. | |
| 2010/0240806 A1 | 9/2010 | Kondo | |
| 2011/0263762 A1 | 10/2011 | Matsuno et al. | |
| 2012/0071590 A1 | 3/2012 | Parssinen | |
| 2012/0090068 A1 | 4/2012 | Glass et al. | |
| 2012/0090759 A1 | 4/2012 | Parssinen et al. | |
| 2012/0171446 A1 | 7/2012 | Park et al. | |
| 2013/0172795 A1 | 7/2013 | Parssinen | |
| 2013/0225731 A1 | 8/2013 | Yin | |
| 2014/0259324 A1 | 9/2014 | Behrend et al. | |

FOREIGN PATENT DOCUMENTS

| | | | |
|---|---|---|---|
| EP | 0765911 A2 | 4/1997 | |
| IE | 20050593 A1 | 3/2006 | |
| JP | S6158192 B2 | 12/1986 | |
| JP | S6255423 B2 | 11/1987 | |
| JP | H0481467 B2 | 12/1992 | |
| JP | H06118460 A | 4/1994 | |
| JP | H08-500748 A | 1/1996 | |
| JP | H09676 A | 1/1997 | |
| JP | H09-137046 A | 5/1997 | |
| JP | 2-733610 B2 | 3/1998 | |
| JP | 2003-165844 A | 6/2003 | |
| JP | 2008-512170 A | 4/2008 | |
| WO | WO 199403211 A1 | 2/1994 | |
| WO | 94/23679 A1 | 10/1994 | |
| WO | 2000/035501 A1 | 6/2000 | |
| WO | WO 2006027763 A2 * | 3/2006 | |
| WO | WO 2007035875 A2 | 3/2007 | |
| WO | WO 2007035875 A2 * | 3/2007 | |
| WO | WO 2007095709 A1 * | 8/2007 | |
| WO | WO 2007095712 A1 * | 8/2007 | |
| WO | WO 2008041215 A1 * | 4/2008 | |
| WO | WO 2008116025 | 9/2008 | |
| WO | WO 2008124035 A2 * | 10/2008 | C08G 63/08 |
| WO | 2010/034689 A1 | 4/2010 | |
| WO | 2010/103186 A2 | 9/2010 | |
| WO | 2010/103187 A2 | 9/2010 | |
| WO | 2012/032226 A2 | 3/2012 | |
| WO | 2013/093843 A1 | 6/2013 | |
| WO | 2015/059355 A1 | 4/2015 | |
| WO | WO 2008041215 A1 | 4/2018 | |

OTHER PUBLICATIONS

Chen, H. C., et al., "Effect of Wood Particle Size and Mixing Ratios of HDPE on the Properties of the Composites," Holz als Roh- under Werkstoff, 2006, 64, 172-177.*
Knife Ring Flakers, PAL, Technical Features. Undated.*
Mesh to micron conversion chart, http://www.showmegold.org/news/Mesh.htm, downloaded Mar. 19, 2014.*
Elias, H.-G., "Plastics, General Survey," Ullmann's Encyclopedia of Industrial Chemistry, published online 2000, vol. 28, pp. 35-154.*
"CAPA for bioplastics," Informational Slides from PERSTORP, 2015, 22 pages.*
Caufield, Clemons, Jacobson, Rowell: "Wood thermoplastic composites"; "13" In: I. Rowell, M. Roger: "Handbook of wood chemistry and wood composites" Jan. 1, 2005, CRC press, XP002608135 isbn: 0849315883, pp. 365-378.
Mortain, Dez, Madec: "development of new composites materials, carriers of active agents, from biodegradable polymers and wood" C.R. Chimie, vol. 7, Jun. 1, 2004, pp. 635-640, XP002608184 DOI: 10.1016/j.crci.2004.03.006.
Sep. 30, 2016 Search Report issued in Great Britian Application No. 1610138.8.
Sep. 30, 2016 Search Report issued in Great Britain Application No. 1610139.6.
Balasuriya, P.W., et al., Mechanical properties of wood flake-polyethylene composites. Part I: effects of processing methods and matrix melt flow behaviour, Composites: Part A 32 (2001) 619-629.
Particle Size Conversion Table. Downloaded from the Aldrich Website on Jan. 22, 2014. Two pages.
Material safety data sheet for CAPA polycaprolactones. Perstorp. 2007.
Trademark registration record for "Lignocel." Registration date of Sep. 8, 1987. Downloaded from the USPTO website on Jan. 23, 2014.

(56) References Cited

OTHER PUBLICATIONS

Nov. 15, 2016 Office Action issued in European Patent Application No. 16173962.8.

* cited by examiner

COMPOSITE MATERIALS COMPRISING A THERMOPLASTIC MATRIX POLYMER AND WOOD PARTICLES

BACKGROUND OF THE INVENTION

Field of Invention

The present invention relates to polymer materials, such as reinforced polymer materials, which are useful as orthopedic materials. In particular, the present invention concerns a composite material comprising a first component formed by a polymer and a second component formed by a reinforcing material. The invention also concerns the use of the polymer materials for casting and splinting.

Description of Related Art

Casting is the most common form of external splinting and it is used for a wide array of bone and soft-tissue injuries. In this context, the function of the cast is to immobilize and to protect the injury and, especially, to minimize motion across a fracture site.

A number of casting materials are known. The first generation of casting material is formed by plaster of paris (in the following abbreviated "POP"). Largely owing to its low cost and ease of molding it has gained universal acceptance. There are, however, a number of disadvantages of POP, including long setting times, messy application, low strength and relative heaviness. Although setting takes only a few minutes, drying may take many hours or days, especially if the atmosphere is moist and cool. Impacts on the plaster while it is setting may cause a weakening of the material. Furthermore, the transparency to X-rays (in the following "radiolucency") is poor.

The second generation of casting materials is formed by synthetic composite materials, such as fiberglass reinforced polyurethane resins. They are useful alternatives to conventional plaster of paris and are gaining increasing popularity. Fiberglass and resinous materials can safely be applied as external splints. These materials are lightweight, durable and waterproof but require protective packaging and they are difficult to apply. Further on, some of the fiberglass casting materials during applying requires special gloves for avoiding penetration of small fiberglass particles through skin. In addition, synthetic casting materials may have a shorter setting and solidification time than traditional plaster-based materials. Further, they are much more expensive than plaster at present, but to balance this disadvantage, fewer bandages are required and they are much more durable in everyday use. They are also more radiolucent than plaster based casting materials.

In cases of fracture a splint, rather than a cast, may be applied in the emergency room. Principally, a splint can be made of the above materials, including plaster and fiberglass, but also from aluminum and moldable plastics. Such a splint is usually wrapped with an elastic bandage and the rigid portion does not envelope the limb circumferentially. It allows for some expansion of the dressing if significant swelling is anticipated. Nonetheless, elevation is just as critical. After an appropriate amount of time, a splint may be replaced by a cast. Both traditional casts and aluminium sheet or foil backed casts must be kept dry during the application and before setting is complete.

Finger splints used for broken or dislocated digits or in tendon injuries are usually made of alumafoam (an aluminium strip padded on one side with sponge-like foam). Sometimes plaster can also be used either alone or in combination with alumafoam.

Casting materials containing fibres or powder of natural substances are known in the art. WO 2007/035875 discloses a cross-linked thermoplastic material with aramide fibres wherein some wood pulp or natural fibres has been incorporated. In WO 94/03211 a composite of saw dust and polycaprolactone is discussed. US Patent Application No. 2008/0103423 concerns a combination of cork and polycaprolactone. The material exhibits some degree of flexibility which allows for some freedom at movements and swelling of the limb.

None of the above discussed materials combine properties of mechanical rigidity, reusability, easy molding and inexpensive price. A further problem is the difficulty to correct the form of the cast after hardening. For the present-day materials, the cast has to be broken up and replaced by a new, if it turns out that the fracture site has been improperly immobilized. The aluminium sheets and foils used in the above-mentioned casts are difficult to recycle and form non-biodegrable medical waste.

SUMMARY OF THE INVENTION

It is an aim of the present invention to eliminate at least a part of the disadvantages of the prior art and to provide a novel material for immobilization of fracture sites in hard- and soft-tissues, in particular in mammals, such as humans.

The present invention is based on the idea of producing a biodegradable orthopedic material having thermoplastic properties. The material is obtained by combining a first polymer component formed by a thermoplastic polymer and a second reinforcing component formed by particles of a biodegradable natural material. The thermoplastic polymer forms the matrix of the material and said particles a discontinuous phase within the matrix.

In particular, the particles comprise finely divided particles of wood or of a similar raw-material, having a granular and in particular generally platy structure. Such particles can be wood chips or a similar raw-material having a granular structure or a generally platy structure. The particles can be capable of being orientated for example within a laminar flow or uniaxial extension of the thermoplastic polymer. The thermoplastic polymer is a biodegradable material (typically a material capable of being broken down especially into innocuous products by the action of living thing and in the presence of water and/or oxygen). Examples of polymers suitable for the present purpose are lactic acid polymer, polylactide, polyglycolide and, in particular, caprolactone homo- or copolymers, the polymer material being selected such that the composite softens when it is heated to a temperature of approximately 50 to 70° C., after which it can be formed directly on the patient.

In another embodiment, the composite material comprises a second component formed by a woody material, the majority of which is being made up of wood particles greater in size than powder.

Thus, the present material can be used as a casting or splinting material.

More specifically, the material according to the present invention is mainly characterized by what is stated in the characterizing parts of claims 1 and 19.

Considerable advantages are obtained by the present invention.

Thus, the splinting material of the present invention can be used in a similar fashion as the known materials. Importantly, in these applications it eliminates many, if not all, of the disadvantages of conventional materials, such as plaster of Paris and synthetic fiberglass reinforced materials.

In a preferred embodiment, the novel wood-plastic composite (WPC) is in toto biodegradable. The material is composed of epsilon caprolactone homopolymer or copolymer or a blend of thermoplastic, biodegradable polymers, optionally combined with conventional thermoplastic materials, and reinforced with discontinuous short length particles of wood or of a similar material, optionally complemented with fibrous materials.

The wood particles orientate in the polymer matrix and provide a self-reinforcement effect. As a result, the present material has good dimensional stability and shaped into a sheet which cannot be easily punctuated under point loading.

The biodegrable thermoplastic material in the composite can be a caprolactone homopolymer, copolymer of different monomers e.g. caprolactone, lactide and/or glycolide or a blend of different homopolymers, e.g. polycaprolactone, polylactide and polyglycolide homopolymers.

The preferred polymer component comprises polycaprolactone which is a biologically acceptable material; some grades even having an FDA approval for internal use in humans. The other component, the woody particles, is also non-toxic. Both of these components are compostable and the novel composite can be used without harm or risk to end-users or patients.

The material of the present invention is ready to be applied for casting or splinting after a warm-up procedure and does not require a messy multistep preparation, like traditional plasters and fiber reinforced resins.

Heating and cooling of the composite can be repeated without changes in the mechanical properties of the material. Therefore, the splint may be remolded and reused on the same patient for the whole recovery time. The total volume of the waste and pollution is therefore diminished.

The material has waterproof and water resistant properties. In one embodiment the material is considered waterproof as it can be heated e.g. in water without causing damage to the material or loosing the geometry of it. In another embodiment the material is considered to have water resistant properties in that it can be cleaned under running water without causing damage to the material or losing its geometry. In either case, the material is considered spill-proof.

In particular, the material of the present invention is moldable at temperatures comfortable against skin and after cooling to the temperature of surroundings it is substantially rigid and slightly flexible so that it comfortably retains its geometry.

When the material is heated close to its melting point, it is possible to attach to it various fastening means (e.g. Velcro) to appliances produced thereof. Naturally any other kinds of straps and hooks and laces can be attached as well, and the surface of the material will readily attach bandage and typical wound care gauze film.

The temperature required for molding lies in the range of about 60 to 70° C. and the thermal conductivity of the material is so low that in clinical use the cast or splint can safely be applied even directly on the skin. At this temperature, the material is soft and pliable and the created form closely matches the anatomical contours of the patient's body or body part.

The splinting material tolerates strong twisting and it can be bent even to relatively sharp, or acute, angles without causing fractures or wrinkles. The wrinkles of splints cause soft tissue damages during long healing process of the fracture and are therefore undesirable.

The splinting material of the present invention is produced from radiolucent components. This is advantageous in fracture fixation applications because the removal of the splint or cast can be avoided when using X-ray imaging.

The material can also be used in manufacturing of orthoses e.g. foot-supporting devices or insoles and sport orthoses devices e.g. shin pad, in which their shock-absorbing properties are particularly useful. They can be plastically deformed and the reinforcement distributes compression and impact forces over a large area. In sport appliances, such as grips for rackets in rackets sports, as well as in the above-mentioned foot-supporting applications, the capability of the material easily to be formed such that it takes up the impression formed by the hand or foot are quite useful. The material can also be used in consumer goods, three-dimensional artwork e.g. jewelry and sculptures, products requiring biodegrading e.g. vessels for plantation.

Next the invention will be examined more closely with the aid of a detailed description and referring to the attached drawings.

DETAILED DESCRIPTION OF PREFERRED EMBODIMENTS

Figure 1:
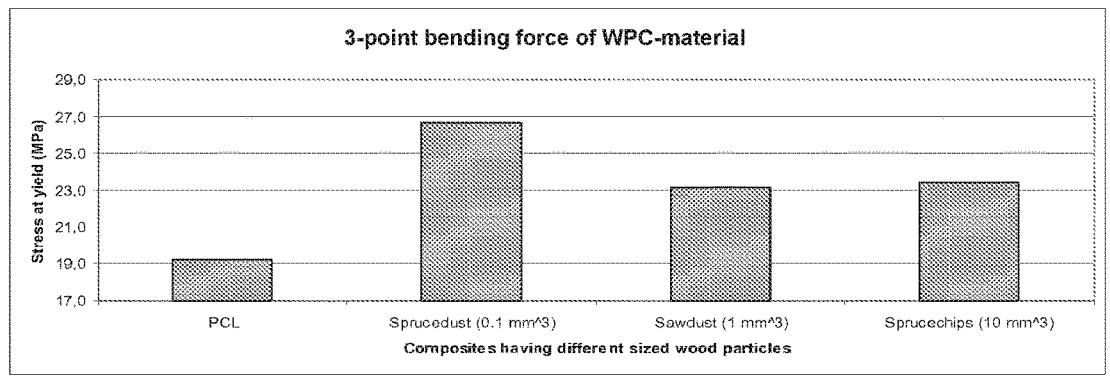
FIG. 1 is a bar chart showing the stress force of test sample in 3-point bending test of wood-PCL composites.

As evident from the above, the material of the present invention can be simply manufactured by mixing the first component, i.e. a suitable polymer material for example in the form of pellets, with the second component i.e. wood particles or granules, by melt mixing. The mixing can be carried out in any conventional apparatus designated for melt mixing or melt processing. One example is a heatable vessel having a mechanical stirrer.

The uniformity of the composite can be increased by using an extruder, kneader or any device suitable for mixing thermoplastic polymers.

By using an extruder mixing apparatus, two hoppers, each containing one of the components of the material, can deposited the desired amount of each component in to the mixing chamber of the apparatus. Then, by way of the mixing means in the mixing apparatus, there is formed a homogeneous mixture of the first and second components prior to the formation of the formation of the material.

One advantage to the material being formed by such a homogeneous mixture of the components is that the forces necessary to form a substantially homogeneous material are reduced. Therefore, little or no compression force is necessary to facilitate mixing of the components in a material formation step. The importance of this factor is that, by way of the homogeneous mixture, larger particles of each component can be used which would otherwise have been destroyed when subjected to high compression forces.

The material can be applied for use after it has been recovered from the mixing device and formed into desired shape for example into a sheet or plate or roll or any similar planar, folded, bent or tubular structure, but the material can even be formed directly on the patient.

The material mixed with an extruder can be shaped with appropriate nozzle to the shape of e.g. rectangular sheet or plate which can be used directly after cutting e.g. as a finger splint.

The desired profile for the splints can be manufactured with the extruder manufactured sheet or plate with e.g. laser cutting, water jet cutting, eccentric pressing or with any tool capable for producing regular shape profiles. The present material can also be process with compression moulding, injection moulding, die-casting, and pressure die-casting.

The sheet or plate can have a thickness of, generally about 1 to 50 mm, in particular about 1.5 to 30 mm, for example 1.5 to 20 mm. A typical thickness is about 2 to 6 mm. The length and the width of the sheet or plate can vary in the range of about 1 to 150 cm (length) and 1 to 50 cm (width), a typical length being about 10 to 60 cm and a typical width being about 5 to 20 cm.

The proportions between the components of the material can vary in a broad range. Thus, generally, 5 to 99 wt-%, for example 40 to 99 wt-%, of the material is formed by the thermoplastic polymer component and 1 to 95 wt-%, for example 1 to 60 wt-%, by the woody material.

The weight ratio of polymer-to-wood can easily be modified and the weight percent of wood, based on the total weight/volume of the composition, may vary between 1 and 70%, preferably however in the range of 10 to 60 weight percent, or 20 to 60 weight percent, and 15 to 50%, or 25 to 50%, by volume.

The second component comprises or consists essentially of a woody material having a smallest diameter of greater than 0.1 mm. As will be discussed below, there can also be other wood particles present in the second component. The woody material can be granular or platy. According to one embodiment, the second component comprises a woody material derived from platy wood particles having a smallest diameter of greater than 0.1 mm.

Thus, generally, the wood component can be characterized generally as being greater in size than powder.

The size and the shape of the wood particles may be regular or irregular. Typically, the particles have an average size (of the smallest dimension) in excess of 0.1 mm, advantageously in excess of 0.5 mm, for example in excess of 0.6 mm, suitably about 1 to 40 mm, in particular about 1.2 to 20 mm, preferably about 1.5 to 10 mm, for example about 1.5 to 7 mm. The length of the particles (longest dimension of the particles) can vary from a value of greater than 1 mm to value of about 1.8 to 200 mm, for example 3 to 21 mm.

The woody particles can be granular, platy or a mixture of both. Woody particles considered to be granular have a cubic shape whose ratio of general dimensions are on the order of thickness:width:length=1:1:1. In practice it is difficult to measure each individual particle to determine if it is a perfect cube. Therefore, in practice, particles considered to be granular are those where one dimension is not substantially different than the other two.

Woody particles considered to be platy means that they have generally a plate-shaped character, although particles of other forms are often included in the material. The ratio of the thickness of the plate to the smaller of the width or length of the plate's edges is generally 1:2 to 1:500, in particular about 1:2 to 1:50. Preferably, the woody particles include at least 10% by weight of chip-like particles, in which the ratio of general dimension are on the order of thickness:width:length=1:1-20:2-100, with at least one of the dimension being substantially different than another.

Based on the above, the platy particles of the present invention generally comprise wood particles having at least two dimensions greater than 1 mm and one greater than 0.1 mm, the average volume of the wood particles being generally at least 0.1 $mm^3$, more specifically at least 1 $mm^3$.

"Derived from platy wood particles" designates that the wood particles may have undergone some modification during the processing of the composition. For example, if blending of the first and second components is carried out with a mechanical melt processor, some of the original platy wood particles may be deformed to an extent.

The majority of wood particles greater in size than powder, which particles may be granular or platy, typically make up more than 70% of the woody material.

The wood species can be freely selected from deciduous and coniferous wood species alike: beech, birch, alder, aspen, poplar, oak, cedar, *Eucalyptus*, mixed tropical hardwood, pine, spruce and larch tree for example.

Other suitable raw-materials can be used, and the woody material of the composite can also be any manufactured wood product.

The particles can be derived from wood raw-material typically by cutting or chipping of the raw-material. Wood chips of deciduous or coniferous wood species are preferred.

As mentioned above, in WO 94/03211 a composite material is described, based upon polycaprolactone, ground almond shell and wood flour. The known material is impaired by several disadvantages, such as a high density of 1.1 $kg/m^3$ or even more, as a result of the small particle sizes of the filler material [wood, less than 600 microns (600 nm)]. Another disadvantage related to the use of small particle sized fillers, is the poor adhesive properties of composite material. According to our experiments (cf. Example 10 below), composites consisting of 40 weight percentage of wood dust sized between 0-800 microns reveal zero adhesion toward bandage material (compression force of 0.1 bars).

To avoid mobilization of the splint and to improve immobilization of the fractured limb during setting of the bandages minor adhesion forces are required. Further on, polycaprolactone polymer (CAPA 656) presented in examples of WO 94/03211 has too low viscosity (melt flow index value of 7 g/10 minutes with 2.16 kg standard die at 160° C.) to be used at practical applying temperature of 65° C. The composite manufactured of PCL having MFI value of seven (PCL-7) tears too easily and does not tolerate strong bending during applying.

By contrast, the present composite materials provide excellent properties also in this respect.

In addition to wood chips and other platy particles, the present composition can contain reinforcing fibrous material, for example cellulose fibers, such as flax or seed fibers of cotton, wood skin, leaf or bark fibers of jute, hemp, soybean, banana or coconut, stalk fibers (straws) of hey, rice, barley and other crops and plants including plants having hollow stem which belong to main class of Tracheobionta and e.g. the subclass of meadow grasses (bamboo, reed, scouring rush, wild *angelica* and grass).

Furthermore, the composition may contain particulate or powdered material, such as sawdust, typically having particles with a size of less than 0.5 mm*0.5 mm*0.5 mm. Particulate or powdered material is characterised typically as material of a size in which the naked eye can no longer distinguish unique sides of the particle. Platy particles are easily recognizable as one dimension is recognizable by the naked eye as being larger than another. Granular particles, while having substantially equal dimensions, are of such dimension that their unique sides can be determined by the naked eye and oriented.

More particularly, particulate or powdered materials are of such a small or fine size that they cannot be easily oriented with respect to their neighbours. Granular and platy particles are of such as size that their sides are recognizable and orientatable.

The desired composition of the second component can be achieved by sifting woody particles through one or more meshes having one or more varying qualities. The desired composition can also be accomplished by other well known techniques in the art for sorting and separating particles in to desired categories. The desired composition may be the resultant composition of one sifting or separating process. The desired composition may also be a mixture of resultant compositions from several sifting or separation processes.

A particularly interesting raw-material comprises wood particles, chips or granules, of any of the above mentioned wood species having a screened size of greater than 0.6 mm up to about 3.0 mm, in particular about 1 to 2.5 mm on an average.

According to one embodiment, the weight ratio of fibrous material (optionally including said powdered material) to the platy material (dry weight) is about 1:100 to 100:1, preferably about 5:100 to 50:50. In particular, the woody material derived from the platy wood particles forms at least 10%, preferably about 20 to 100%, in particular about 30 to 100%, of the total weight of the second component.

The woody material makes up at least and preferably more than 70% of the second component.

In addition to wood-based powdered materials, inorganic particulates or powdered materials such as mica, silica, silica gel, calcium carbonate and other calcium salts such as tricalcium orthophosphate, carbon, clays and kaolin may be present or added.

According to an alternative, a composite useful as an orthopedic material, comprises a first component formed by a polymer and a second component formed by a reinforcing material, wherein the first component comprises a thermoplastic polymer selected from the group of biodegradable polymers and mixtures thereof, and the second component comprises reinforcing fibres. Such fibers can be selected from the group for example of cellulose fibers, such as flax or seed fibers of cotton, wood skin, leaf or bark fibers of jute, hemp, soybean, banana or coconut, stalk fibers (straws) of hey, rice, barley and other crops including bamboo and grass. According to an interesting embodiment, the wood filler may consist of or consist essentially of fibres of the indicated kind. The polymer component can be any of the below listed polymers, caprolactone homo- or copolymers having a molecular weight of about 60,000 g/mol or 65,000 g/mol up to 250,000 g/mol being particularly preferred.

The thermoplastic polymer and its properties will be discussed in more detail below, but for the sake of order it is pointed out that in all of the above mentioned embodiments, wherein various fillers are used as a second and a third and even fourth component of the composition, substantial advantages with respect to biodegradability and mechanical properties have been found using caprolactone polymers, in particular homopolymers, as thermoplastics. The particularly preferred polymer component is a caprolactone homopolymers having a molecular weight of above 80,000 g/mol. Specifically, caprolactone having a molecular weight of between 100,000 g/mol and 200,000 g/mol as been found to be advantageous both in terms of resultant properties and cost.

Before the woody particles are mixed with the thermoplastic polymer they can be surface treated, e.g. sized, with agents, which modify their properties of hydrophobicity/hydrophobicity and surface tension. Such agents may introduce functional groups on the surface of the granules to provide for covalent bonding to the matrix. Even increased hydrogen bonding or bonding due to van der Waals forces is of interest. The woody particles can also be surface treated with polymer e.g. PCL having low viscosity and molar mass values to increase holding powers between wood and PCL having high viscosity value.

The wood material can be also coated or treated with anti-rot compound e.g. vegetable oil to improve its properties against aging and impurities.

The wood material can be dehydrated to make it lighter before mixing it with polymer. The mechanical and chemical properties of wood material can be improved with heat treatment, which is known to decrease e.g. swelling and shrinkage.

In the composition according to an aspect of the present invention, the first component (the polymer) forms the matrix of the composite, whereas the microstructure of the second component in the composition in discontinuous. The particles of the second component can have random orientation or they can be arranged in a desired orientation. The desired orientation may be a predetermined orientation.

As mentioned above, according to a preferred embodiment, a polycaprolactone polymer (in the following also abbreviated "PCL") is used as a thermoplastic polymer in the first component of the composition. The polycaprolactone polymer is formed by repeating units derived from epsilon caprolactone monomers. The polymer may be a copolymer containing repeating units derived from other monomers, such as lactic acid, glycolic acid, but preferably the polymer contains at least 80% by volume of epsilon caprolactone monomers, in particular at least 90% by volume and in particular about 95 to 100% epsilon caprolactone monomers.

In a preferred embodiment, the thermoplastic polymer is selected from the group of epsilon-caprolactone homopolymers, blends of epsilon-caprolactone homopolymers and other biodegradable thermoplastic homopolymers, with 5-99 wt %, in particular 40 to 99 wt %, of an epsilon-caprolactone homopolymer and 1-95 wt %, in particular 1 to 60 wt %, of a biodegrable thermoplastic polymer, and copolymers or block-copolymers of epsilon-caprolactone homopolymer and any thermoplastic biodegrable polymer, with 5 to 99 wt %, in particular 40 to 99 wt % of repeating units derived from epsilon-caprolactone and 1 to 95 wt %, in particular 1 to 60 wt %, repeating units derived from other polymerizable material.

Examples of other biodegradable thermoplastic polymers include polylactides, poly(lactic acid), polyglycotides as well as copolymers of lactic acid and glycolic acid.

The first polymer component, in particular the epsilon caprolactone homo- or copolymer, has an average molecular weight of 60,000 to 500,000 g/mol, for example 65,000 to 300,000/mol, in particular at least 80,000 g/mol, preferably higher than 80,000 and up to 250,000.

The molding properties of the present invention can be determined by the average molecular weight ($M_n$) of the polymer, such as epsilon caprolactone homo- or copolymer.

A particularly preferred molecular weight range for the $M_n$ value of PCL is from about 100,000 to about 200,000 g/mol.

The number average molar mass (Mn) and the weight average molar mass (Mw) as well as the polydispersity (PDI) were measured by gel permeation chromatography. Samples for GPC measurements were taken directly from the polymerization reactor and dissolved in tetrahydrofuran (THF). The GPC was equipped with a Waters column set styragel HR(1, 2 and 4) and a Waters 2410 Refractive Index Detector. THF was used as eluent with a flow rate of 0.80 ml/min at a column temperature of 35° C. A conventional polystyrene calibration was used. In determination of the water content of the monomer at different temperatures a Metroohm 756 KF Coulometer was used.

The properties of moldability of the present composition can also be determined by the viscosity value of the polymer. For an epsilon caprolactone homopolymer: when the inherent viscosity (IV)-value of PCL is less than 1 dl/g the composite is sticky, flows while formed and forms undesired wrinkles while cooling. When PCL having IV-value closer to 2 dl/g is used the composite maintains its geometry during molding on the patient and it may be handled without adhesive properties. Thus, IV values in excess of 1 dl/g are preferred, values in excess to 1.2 dl/g are preferred and values in excess of 1.3 dl/g are particularly suitable. Advantageously the values are in the range of about 1.5 to 2.5 dl/g, for example 1.6 to 2.1 dl/g. Inherent Viscosity values were determined by LAUDA PVS 2.55 d rheometer at 25° C. The samples were prepared by solvating 1 mg of PCL in 1 ml chloroform ($CH_3Cl$).

A particularly important feature of the thermoplastic polymer is the viscosity which is relatively high, typically at least 1,800 Pas at 70° C., 1/10 s; the present examples show that the viscosity can be on the order of 8,000 to 13,000 Pas at 70° C., 1/10 s (dynamic viscosity, measured from melt phase). Below the indicated value, a reinforced material readily wrinkles during forming it on a patient.

The thermoplastic material is preferably a biodegradable polymer (only) but also non-biodegradable polymers may be utilized. Examples of such polymers include polyolefins, e.g. polyethylene, polypropylene, and polyesters, e.g. poly(ethylene terephthalate) and poly(butylenes terephthalate) and polyamides. Combinations of the above biodegradable polymers and said non-biodegradable polymers can also be used. Generally, the weight ratio of biodegradable polymer to any non-biodegradable polymer is 100:1 to 1:100, preferably 50:50 to 100:1 and in particular 75:25 to 100:1. Preferably, the composite material has biodegradable properties greater, and the material biodegrades quicker or more completely, than the thermoplastic material alone.

According to the invention, a polymer of the afore-said kind is preferably moldable at a temperature as low as +50° C., in particular at +65° C. or slightly above, and it can be mixed with wood particles or generally any porous material gaining increased rigidity of the formed composite. The polymer component, such as polycaprolactone homopolymer, defines the form of the splinting material against the skin.

The modulus (Young's modulus), at ambient temperature, of the polymer component is greater than 300 MPa. By compounding the polymer with the wood component, the modulus will be improved (cf. below), typically it is about 350 to 2000 MPa for the composition.

The present material contains a significant portion of wood granules having a particle size greater than the micrometer range, for example a size of about 0.75 mm to 50 mm. When the material is shaped into a sheet, (at least most of) the wood granules become oriented in two dimensions within forming of the thermoplastic material into sheets.

According to a preferred embodiment, the present method of producing a composite useful as an orthopedic material comprises the steps of mixing together 10 to 100 parts, preferably 50 to 100 parts, by weight of a first component formed by a polymer selected from the group of biodegradable polymers and mixtures thereof, and 1 to 100 parts, preferably 10 to 50 parts, by weight of a second component formed by a reinforcing material, present in the form of platy wood particles.

The mixing can be melt mixing carried out at a temperature sufficient for melting the thermoplastic polymer, e.g. at about 50 to 150° C. Alternatively, the temperature can be in the range of about 80 to 190° C., preferably about 100 to 150° C.

The molten polymer mass containing a mixture of biopolymer and reinforcing platy or granular particles can be shaped manually or, according to a preferred embodiment by moulding in a mould.

The molten polymer mass can be subjected to tensile forces to achieve a desired orientation of the polymer and, in particular, the reinforcing particles.

The manufacturing process can, on an industrial scale, be carried out as follows:

In a first step wood chips or granules and plastic granules are mixed to form a uniform blend before pouring into the feed hopper of an extruder. The mixing process can be carried out also by feeding of the virgin materials to the extruder directly by using separate feeding hoppers.

The compounding is then carried out in, e.g., an extruder, in particular a single screw extruder. In the compounding process the screw extruder profile of the screw is preferably such that its dimensions will allow relatively large wood chips to move along the screw without crushing them. Thus, the channel width and flight depth are selected so that the formation of excessive local pressure increases, potentially causing crushing of the wood particles, are avoided. The temperature of the cylinder and the screw rotation speed are also selected such as to avoid decomposition of wood chip structure by excessively high pressure during extrusion. For example a suitable barrel temperature can be in the range of about 110 to 150° C. from hopper to die, while the screw rotation speed was between 25-50 rpm. These are, naturally, only indicative data and the exact settings will depend on the actual apparatus used.

The compounded composite material obtained from the melt processing/compounding step is then profiled in the tool to a homogeneous product, e.g. a sheet or plate, for example using suitable mechanical processing. One particularly suitable method is calendaring. Another suitable process is by pressing.

To avoid changes in the structure of the wood material during mechanical processing, the composite material can be subjected to gentle folded between the processing steps.

Usually, the mechanical processing is carried out at a temperature well above the glass transition/melting point of the polymer.

The density of composite manufactured typically lies in the range of about 600 to 850 kg/m³, depending on the weight percent of wood in material.

The manufacturing process is described in more detail in our co-pending patent application titled "Method of Producing a Composite Material", the content of which is herewith incorporated by reference.

The composite retains its shape as it cools down. It is substantially rigid but flexible so as to be supportive and comfortable. Rigidity is generally achieved when a sample heated to the above indicated softening temperature is cooled to below 50° C., in particular to less than 45° C., preferably less than 40° C. Typically, the composite is rigid at ambient temperature, a suitable temperature of use is about 20 to 50° C., in particular 22 to 40° C.

The reinforced material typically exhibits properties selected from one or several of the following:
- a density of the composition is at least 5% less than that of the polymer component (e.g. epsilon-caprolactone homopolymer) as such;
- a Young's modulus value in 3-bending test of the composition is at least 10% higher than that of the polymer component (e.g. epsilon-caprolactone homopolymer) as such; and
- a thermal conductivity on the order of about 0.5 W/m·K, at the most.

At a manipulation temperature of 50 to 70° C., typically about +65° C. or slightly more, the splinting material can be manipulated and manually shaped for up to 10 minutes and it is typically pliable for 3-10 minutes after the finishing of heating, depending of the size of splint. The material hardens entirely in one hour. Operation time of the melt material can be expanded by heating the material close to +100° C., which is the temperature limit for the material to be handled without protective gloves. The material can be heated to +150° C. and held there for several hours without changes in the material properties.

To achieve rapid solidification of the material, a cooling spray or a cooling gel or wrap can be used.

As mentioned above, and as will be discussed below in connection with the examples, the present composition can be used as a composite material according to any of the preceding claims for use as an orthopedic material. Such materials are exemplified by finger splints, wrist casts and ankle casts. Generally, the platy particles form about 30 to 70%, preferably in excess of 40 up to about 60%, of the total weight of the composition, for finger splints and for ankle casts about 20 to 60%, preferably about 30 to 50% of the total weight of the composition. There is typically a greater portion of the larger particles present in the larger casts which will reduce the total weight of the cast without impairing the strength properties thereof.

In particular, the composite material of the present invention is manufactured in to either a blank or in to a desired, specific shape or form. Ideally, the blanks and forms are linier, two dimensional and easily stackable. The blanks can be either substantially larger than the intended size to be applied to the animal or human being, herein referred to as the patient, or of substantially similar size.

In the instance when the blank is of a large size than desired, the blank can be cut with normal scissors or other conventional cutting means before application. Such a large blank is preferable in the sense that one blank may be cut in to several splints at various times according to the size required by each. Therefore, it is not necessary to store many different shapes and sizes of the material, which take up room and may be rarely used.

Additionally, multiple splints may be cut from one blank in such a way as to maximize the material used and not produce a large amount of waste product.

Once the proper size and shaped piece of material is obtained, cut or selected, the material is then heated to the desired operating temperature by a heating means. Numerous heating means are known in the art, but it is preferable to uniformly heat the material to a specific desired temperature. If the temperature is too high then there is risk of discomfort or harm to the patient's skin. If the temperature is not high enough then the material will not be able to properly conform to the patient's body.

Therefore, in one embodiment, the composite materials are provided along with a heater which is specifically tailored to the application of the composite materials. The heater may have an adjustable thermostat or may be pre-programmed to heat automatically to the desired temperature. Ideally, the heater will have a heating element capable of heating an entire blank or form of the composite material evenly and completely. The size of the heater should be sufficient enough to handle the size of the composite materials to be used. The heater may be given complimentary along with complementary or paid composite material blanks or forms to entice people to use the system and material.

In cases where the heating element is other than one specifically tailored to the present composite material it can be selected from the range of known heating elements including contact heaters, convection heaters, chemical heating and the like.

Once the composite material blank or form is heated to the desired temperature, as discussed above, then the material can be placed on the patient in the desired location to form the exo-skeletal device. The advantage of the present material is that it can be handled by hand without any protective requirement such as gloves. Equally important is that the material can be formed directly against the patient's skin. However, it can be advantageous to have some material, such as gauze or other cloth/cloth like material, directly in contact with the patient's skin and to form the composite material over that material.

With the composite material still pliable and moldable, it can be fit to contour the patient's body part nearly or exactly. Additionally, if the initial placement is not desirable, the material can be moved while still moldable to a more desirable location. If the material has lost its desired moldability, then it can be reheated and likewise moved to the new location. One of the particular advantages of the present material is that it can be heated and cooled many times without degrading its mechanical properties.

When the composite material is located properly and molded to the desired form, then it can be allowed to cool to a temperature where it can be removed but maintain its shape. The cooling may be accomplished by allowing the ambient conditions to reduce the temperature of the material or the cooling may be aided by spraying the material with water or another chemical to speed up the cooling. Additionally, solid cooling means can be used to cool the material such as a cold pack or ice place directly against the composite material.

The use of the present material as a splint or cast process is described in more detail in our co-pending patent application titled "Orthopaedic Splinting System", the content of which is herewith incorporated by reference.

The following non-limiting examples illustrate the invention.

In all the below presented examples, the polycaprolactone polymer used was a commercially available PCL homopolymer supplied under the tradename CAPA 6800 by Perstorp Ltd., Sweden). The polycaprolactone has a melt flow rate of about 3 g/10 min (measured at 150° C. and with a weight of 2.16 kg) and referred to as "PCL-3". As mentioned above, another caprolactone homopolymer also used had a significantly higher melt flow rate of about 7 g/10 min (referred to as "PCL-7").

The wood material, if not otherwise indicated, was conventional spruce chips produced at a Finnish saw mill. In some of the examples wood particles of other wood species were used. The chips, in particular the spruce chips, were occasionally used in the form of a fraction sieved to an average size of 1-2.5 mm.

Example 1

78 grams of the commercially available PCL with a molecular weight in the range of approximately 120-150 000 g/mol and 22 grams of cubic sawmill spruce chips of average dimensions 2.4×2.7×1.9 mm were mixed and poured on a release paper and heated in oven at 100 degrees for approximately 60 minutes. After melting of polymer was observed, the wood-PCL mixture was removed from oven and folded to shape of a thick plate (thickness 4-5 mm). After solidifying, the composite plate was placed back to the oven and allowed to re-melt. The melting and shaping cycle was repeated until a homogenous distribution of components was achieved.

Example 2

85 g of ε-polycaprolactone CAPA 6800 and 24 g of large aspen chips with average dimensions of 4.8×5.6×1.2 mm were melted to a wood-PCL composite according to preparation method in Example 1. A light-weight composite plate with optimum flexibility and rigidity for orthopaedic casts was received.

Example 3

77 g of ε-polycaprolactone CAPA 6800 and 33 g of fine sawdust of mixed wood qualities (spruce, pine and birch) were melted and mixed according to preparation method described in Example 1 to achieve desired wood-PCL composite.

Example 4

700 g of ε-polycaprolactone CAPA 6800 and 300 g of sprucedust with average dimensions of 2×2×0.2 mm and were fed separately into a hopper of a Gimac mini twin-screw extruder. Temperatures of screw, adapter and nozzle were close 130 deg C. The composite blend was pushed out through the compounder nozzle (diameter 4 mm) and collected to the rolling belt. The composite was cooled down by pressurized air while moving on the belt. As a result a cylinder shaped homogenous mixture of wood particles and polymer was received. Test samples for the mechanical tests were prepared according to method described in Example 1.

The sizes of the wood particles used for the preparation of the wood-PCL composites presented in Examples 1 to 4 are listed on the following Table 1. The dimensions of wood particles presented in Table 1 describe only average size wood material.

Table 1.

TABLE 1

| wood quality | dimensions of individual wood particle (1 × w · × t) (mm) | approximate volume of individual wood particles (mm³) |
| --- | --- | --- |
| spruce chips | 2.4 × 2.7 × 1.9 | ~10 |
| aspen chips | 4.8 × 5.6 × 1.2 | ~30 |
| sawdust | n.d. | ~0.1 |
| sprucedust | 2 · × 2 × 0.2 | ~1 |

Example 5

The influence of the reinforcing component on mechanical properties was studied with the 3-point bending test. The flexural strengths and modulus of the composites were measured with universal testing machine Instron 4411. A pure PCL, without any reinforcement was used as control.

Figure 2:
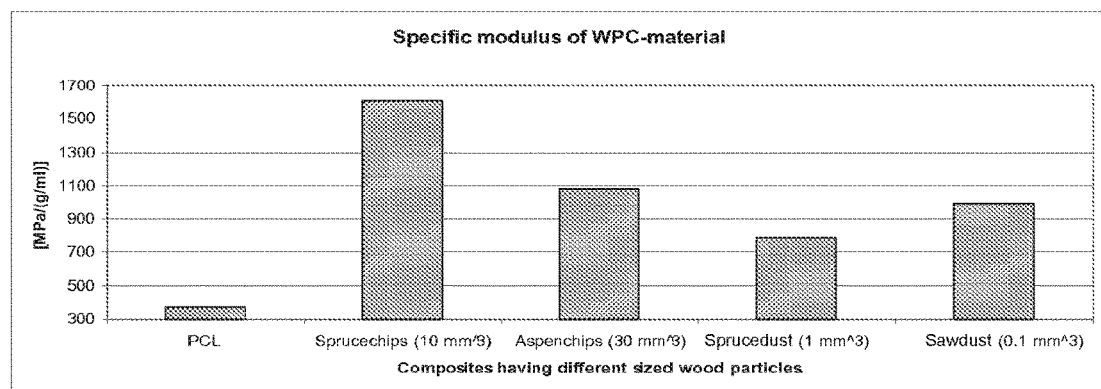
FIG. 2 is a graphical representation of the specific modulus (E/p) of test sample in 3-point bending test.

The test samples (dimensions 55×10.5×5.5 mm) were prepared by mixing constant ratio of different size wood chips (30 weight %) and ε-polycaprolactone homopolymer (70 weight %) and pressed into a Teflon mould. The melting and shaping of samples until a homogenous distribution of components was achieved. The samples were tested by constant cross head speed of 10 mm/min. The 3-point bending forces are presented graphically in FIG. 1 and Young's modulus of elasticity in FIG. 2.

Example 6

Figure 3:
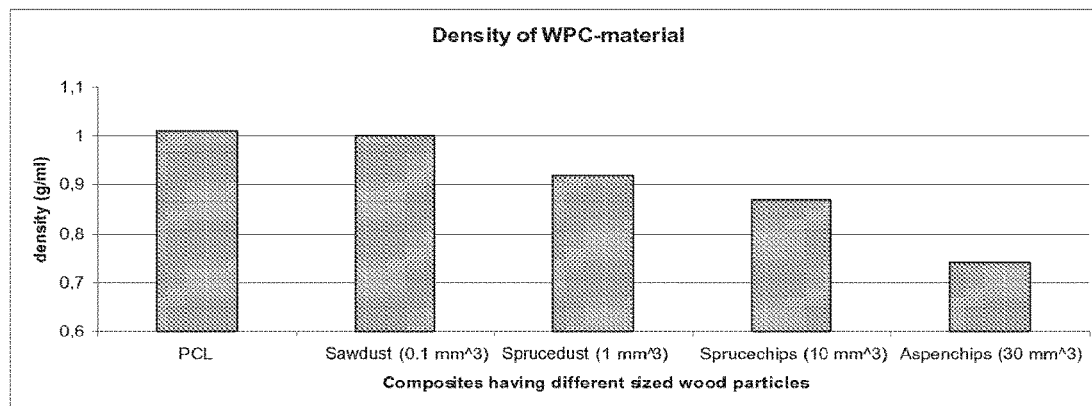
FIG. 3 shows the densities of composites having different sized wood particles.

The densities of the samples prepared in Example 5 for mechanical testing were measured by determining the dimensions of the regular size samples and weighting them. The densities of the composites are graphically presented in FIG. 3. As will appear, composites according to the present invention have a considerably smaller density than polycaprolactone as such.

Example 7

The composite material prepared in the Example 3 was tooled into a plate suitable for making a splint cast to support finger (a "finger splint").

Approximately 5 grams of composite material was cast to a plate at 100° C. and allowed to cool down. The composite was re-heated up to 70° C. and when still warm and moldable (above 65° C.) the cast composite was manipulated with the help of roller pin to form of a plate, thickness approximately 2 mm. The size of received composite plate was 35×60 mm.

Figure 4:
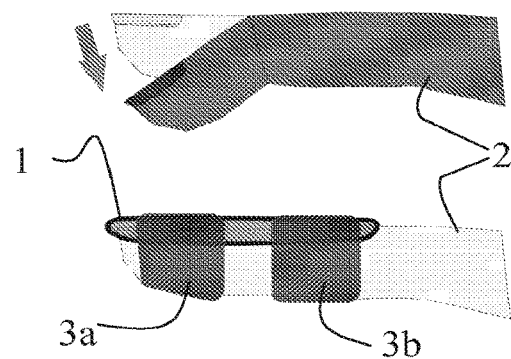
FIG. 4 shows in a schematic side-view the use of the present material as a cast for treating ruptures of the extensor tendon in a the first finger joint.

FIG. 4 shows the use of the finger splint. The upper drawing illustrates an injured (mallet) index finger 2 which has a rupture of the extensor cordon. As will appear, the composite plate 1 can be applied directly on the dorsal side of the mallet finger 2. The composite plate can shaped to contour the finger so that the palmar side of finger is left open. Upon cooling the composite splint solidifies. Cooling was accelerated with a wet tissue. After cooling, ordinary bandage (strips 3a and 3b) can be added to immobilize the treated finger.

When removing the composite cast 1, a smooth surface inside the splint is observed having no wrinkles or other irregular shapes causing irritation of skin.

Example 8

Figure 5:
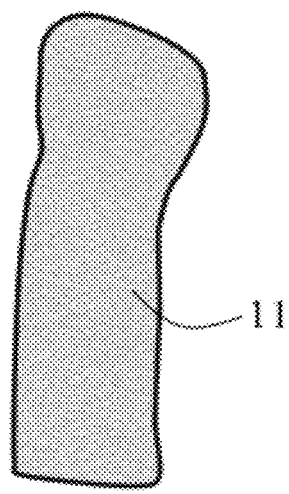
FIG. 5 shows a schematic fashion a front-view of a reshapable wrist cast.

This example describes the production of a re-shapable wrist cast 11 having the general shape shown in FIG. 5.

Approximately 100 grams of composite material prepared in Example 1 was cast onto a metal plate and release paper at 100° C. and allowed to cool down. The composite was re-heated up to 70° C. and when still warm and moldable the cast composite was manipulated to form of a thick plate, thickness approximately 6 mm. Excess of materials was cut away with scissors when still warm. The cut edges were gently contoured by hand in order to soften the sharp edges. The size of received composite plate was 12×25 cm.

The composite plate was applied directly on repositioned wrist. The composite plate was left open on medial side of wrist. The wrist was kept repositioned until the cast had solidified.

The semi-open wrist cast can be easily removed and re-shaped if after imaging the clinician need to the repair the resulted repositioning of wrist bones. The wrist cast may be re-softened at the oven heated to 70° C. or in water bath and replaced in the corrected position on the wrist.

Example 9

This example illustrates the preparation of an anatomic ankle cast and the application thereof 200 grams of composite material manufactured in the Example 2 was cast on release paper at 100° C. and allowed to cool down. The composite was re-heated up to 70° C. in heat oven to resemble a thick plate, thickness approximately 8 mm. The received composite plate, dimensions 15×40 cm was cut to anatomical shape with scissors when it was still warm.

Especially area that is needed for the medical personnel to hold the leg when repositioning the ankle was cut slightly open. Also, extra strips were cut to be later attached on the anterior side of the cast. The cut edges were gently contoured by hand in order to soften the sharp edges.

Figure 6:
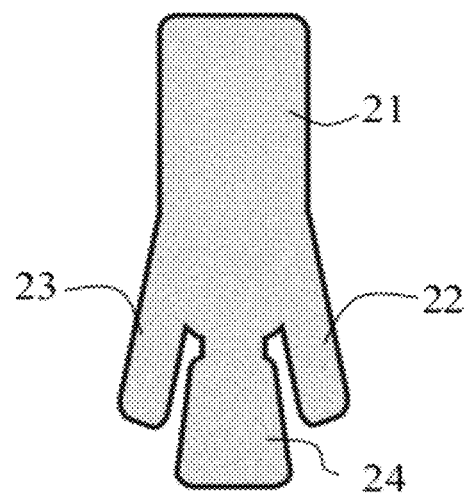
FIG. 6 shows in a schematic fashion a front-view of an anatomic ankle cast according to an embodiment of the invention.

FIG. 6 shows the general form of the produced cast plate. Reference numeral 21 refers to the cast plate and numerals 22 to 24 to foldable flaps.

Figures 7A, 7B:
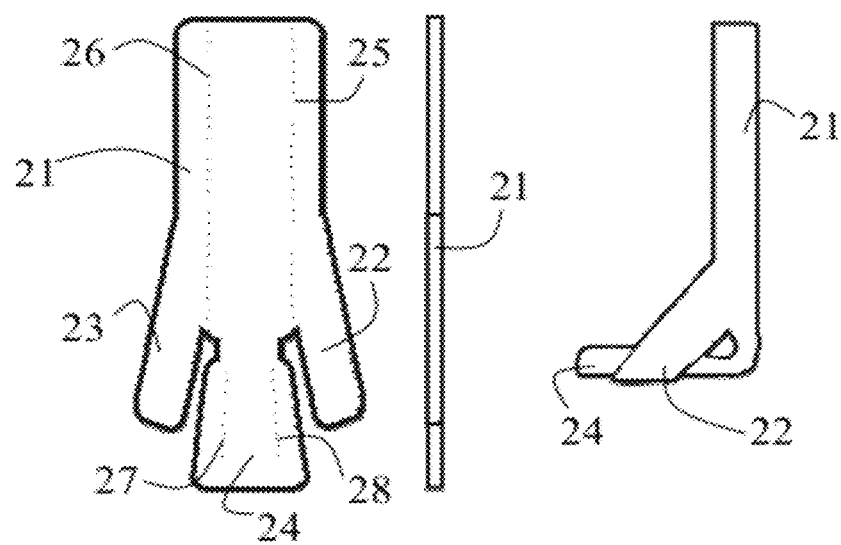
FIG. 7a shows the front and side views of an unfolded anatomic ankle cast of the kind depicted in FIG. 6.
FIG. 7b shows the side view of the same cast in folded position.

FIGS. 7a and 7b show how the composite plate 21 can be reshaped when applied directly on the leg during repositioning of the ankle after an injury.

Thus, in the application, the leg is kept repositioned until the cast has solidified. When still warm, the cut flaps 22 and 23 are folded along folding lines 25 and 26 and compressed gently on the anterior side of the composite cast. The cut flap 24 can in a similar fashion be bent and shaped by folding its side portions along folding lines 27 and 28. The material is non-tack but it grips well with itself when it is still moldable, i.e. above 65° C.

Example 10

This example illustrates how a test according to the peel adhesion test method shows the relative bond strength of a given tape/bandage to surface (material and texture) of composite splint. A molten WPC-material can be considered to be a pressure sensitive adhesive. In this test gauze bandage is pressed with steel slab surface of molten composite for 30 seconds and allowed to cool to RT. After hardening of the composite gauze is peeled off at a 180° angle from substrate at a constant peel rate by using Instron mechanical testing device. The measurements were carried out according to the modified standard SFS-EN 1939 (Standard Test Method for Peel Adhesion of Pressure-Sensitive Tape).

A composite plate (width·length·thickness=60 mm··90 mm··3.5 mm) was placed into oven and allowed to set at a temperature of 65° C. during 30 minutes. After heating procedure the composite plate was removed from the oven followed by pressing a strip of elastic gauze bandage (width 50 mm, length ~250 mm, thickness 0.6 mm) to composite plate using a 3.3 kg weight (0.09 bar). The gauze is folded twice on the composite plate so that area size of w·1=60 mm·20 mm·3.1 mm) is free. After 30 seconds of pressing the slab is removed and the composite/gauze assembly was allowed cool down to room temperature. After cooling the system was placed into Instron testing machine. The loose end of the strip was connected to the peel arm and the composite plate was mounted horizontally onto a stage allowing ~180° angle to be maintained as the tape was pulled from the surface of the composite (FIG. 8). The rate of peeling was kept constant at 50 mm/min. The peeling force as a function of distance was collected. The peeling is ended before the last 20 mm of the test specimen is achieved.

The composite manufactured of PCL-7 and small wood particles in weight ratio of 60:40 (particle size between 0-0.8 mm) revealed zero adhesive force. After changing the wood particles to larger ones (particle size between 1 mm-5 mm) an adhesion force in the range of 1 to 50 N was detected. This force is sufficient for adhering the bandages to the surface to avoid sliding of them when applying the splint on a patient. When the large wood particles were combined with high molar mass polycaprolactone in weight ratio of 70:30 adhesion force of 23 N was achieved.

It is worth mentioning that PCL-7 as such had an adhesive force of 197 N. The adhesion is very strong and the gauge bandage cannot be anymore removed by hands from the polymer sample.

Example 11

Spruce chips were dried for 4 hours in 120° C. and polymer granules were used as received. Preliminary mixing of virgin materials was carried out in a sealed plastic vessel. The mixture (200 g wood chips/300 g PCL granules) was poured to the feed hopper connected to a Brabender single-screw extruder with four heating zones. The rotational speed of the extruder was set to 50 rpm and the temperatures of all four zones were fixed at 130° C. After compounding process with the extruder, the formed composite material was heated in an oven to 125° C. to ensure its easy mouldability during the following calendering process. The calendering of composite mixture to a homogeneous plate was carried out in three phases which all included several cycles, folding, cooling and reheating steps. The temperature of calender cylinder was fixed at 100° C. After calendering process the plate-like composite was cut with band-saw to size of 10 cm by 40 cm followed by one cycle calendering at 100° C. to achieve smooth surface to casting material.

The invention claimed is:

1. A composite material, comprising
   a first component including polycaprolactone having a melt flow index of less than 7 g/10 min, and
   a second component including a woody material in the form of platy wood particles, the platy wood particles having a thickness, a width and a length such that a ratio of the thickness of the platy wood particles to the smaller of the width or the length of the platy wood particles is between 1:2 and 1:500, wherein the composite material has a density of 0.74 g/mL to 0.92 g/mL, and a specific modulus of 800 MPa/(g/mL) to 1080 MPa/(g/mL).

2. The composite material according to claim 1, wherein the first component forms a matrix of the composite, and a microstructure of the second component is discontinuous.

3. The composite material according to claim 1, wherein the composite material is formable at a temperature of approximately 50 to 70° C. and being rigid at a temperature of less than 50° C.

4. The composite material according to claim 1 arranged in the form of a finger splint, a wrist cast or an ankle cast.

5. The composite material according to claim 1, comprising:
    5 to 99 parts by weight of the polycaprolactone, and
    1 to 95 parts by weight of the woody material, the weight of the woody material being calculated based on the dry weight of said woody material.

6. The composite material according to claim 1, wherein the woody material in the form of the platy wood particles forms at least 10% of the total weight of the second component.

7. The composite material according to claim 1, wherein the average size of the smallest dimension of the platy wood particles is at least 0.5 mm.

8. The composite material according to claim 1, wherein the thickness of the platy wood particles is greater than 0.1 mm.

9. The composite material according to claim 1, wherein the individual wood particles have at least two dimensions greater than 1 mm and one greater than 0.1 mm, said wood particles having an average volume of at least 1 mm$^3$.

10. The composite material according to claim 1, wherein the wood particles are arranged such that six surfaces of the particles is visually viewable.

11. The composite material according to claim 1, wherein the wood particles comprise chips of hardwood, softwood or a combination thereof.

12. The composite material according to claim 1, wherein the wood particles are orientated and aligned in a melt flow of the polymer.

13. The composite material according to claim 1, wherein
    the second component includes another particulate material that is different from the platy wood particles, a fibrous material or a combination thereof, and
    the another particulate material, the fibrous material or the combination thereof being approximately 1% to 15% of the weight of the second component.

14. The composite material according to claim 1, wherein the polycaprolactone is selected from the group of epsilon-caprolactone homopolymers, and blends of epsilon-caprolactone homopolymers with other biodegradable thermoplastic homopolymers, with 5-99 wt % of an epsilon-caprolactone homopolymer and 1-95 wt % of a biodegrable thermoplastic polymer, and copolymers of epsilon-caprolactone homopolymer and any thermoplastic biodegrable polymer, with 5 to 99 wt % of repeating units derived from epsilon-caprolactone and 1 to 95 wt % repeating units derived from other polymerizable material.

15. The composite material according to claim 1, wherein the polycaprolactone has an average molecular weight of approximately 100,000 to 200,000 g/mol.

16. The composite material according to claim 1, wherein the first component has an inherent viscosity in excess of 1 dl/g.

17. A composite material comprising:
    a first component including a polycaprolactone having an inherent viscosity between 1.0 dl/g to 2.5 dl/g, and
    a second component including a woody material including platy wood particles having a thickness, a width and a length such that a ratio of the thickness of the platy wood particles to the smaller of the width or the length of the platy wood particles is between 1:2 and 1:500, wherein
    the composite material has a density of 0.74 g/mL to 0.92 g/mL, and a specific modulus of 800 MPa/(g/mL) to 1080 MPa/(g/mL).

18. The composite material according to claim 17, wherein the platy wood particles make up more than 70% of the woody material.

19. The composite material according to claim 18, wherein
    the polycaprolactone is in pellet form and has dimensions similar to those of the woody material granular particles, and
    the first and second components in the composite material is homogeneous.

20. The composite material according to claim 17, wherein the thickness of the platy wood particles is greater than 0.1 mm.

21. The composite material according to claim 17, wherein the woody material includes substantially granular particles having a cubic shape with dimensions from greater than 0.6 mm up to approximately 3.0 mm.

22. The composite material according to claim 21, wherein the woody material comprises granular particles having an average, sieved size of greater than 0.6 mm up to approximately 3.0 mm.

23. A blank for use as an orthopedic splint after molding of the blank, the blank comprising:
    a structure in a form of a plate, sheet, a roll, or a planar, folded, bent or tubular structure, the structure being formed of a composite material that is moldable at a temperature above 50° C., the composite material including:
        polycaprolactone polymer having a melt flow index of less than 7 g/10 minutes; and
        platy wood particles orientated in two dimensions of the structure, the platy wood particles having a thickness, a width and a length such that: a ratio of the thickness of the platy wood particles to the smaller of the width or the length of the platy wood particles is between 1:2 and 1:500, wherein
        the composite material has a density of 0.74 g/mL to 0.92 g/mL, and a specific modulus of 800 MPa/(g/mL) to 1080 MPa/(g/mL).

24. The blank according to claim 23, wherein the ratio of the thickness of the platy wood particles to the smaller of the width or the length of the platy wood particles is between 1:2 and 1:50.

25. A blank for use as an orthopedic splint after molding of the blank, the blank comprising:
    a linear structure in a form of a plate, sheet, a roll, or a planar, folded, bent or tubular structure, the linear structure being formed of a composite material that is moldable at a temperature above 50° C., the composite material including:
        polycaprolactone polymer having a melt flow index of less than 7 g/10 minutes; and
        platy wood particles orientated along an axis parallel to a length of the linear structure, the platy wood particles having at least two dimensions greater than 1 mm, and one dimension greater than 0.1 mm, the platy wood particles having an average volume of at least 1 mm³, wherein the composite material has a density of 0.74 g/mL to 0.92 g/mL, and a specific modulus of 800 MPa/(g/mL) to 1080 MPa/(g/mL).

26. A method for manufacturing a composite material, the method comprising:

mixing a polycaprolactone polymer having a melt flow index of less than 7 g/10 min with woody materials including platy wood particles and granular wood particles, wherein:

the platy wood particles have a thickness, a width, and a length such that: a ratio of the thickness of the platy wood particles to the smaller of the width or the length of the platy wood particles is between 1:2 and 1:500, and the composite material has a density of 0.74 g/mL to 0.92 g/mL, and a specific modulus of 800 MPa/(g/mL) to 1080 MPa/(g/mL).

27. The method according to claim 26, wherein the mixing is carried out at a temperature of approximately 50° C. to 190° C. in order to achieve conditions of melt-mixing in an apparatus.

* * * * *